United States Patent [19]

Hall et al.

[11] Patent Number: 5,985,252
[45] Date of Patent: Nov. 16, 1999

[54] COSMETIC COMPOSITION

[75] Inventors: Lynne Hall, Pocklington; Gordon Charles Hough, Chester, both of United Kingdom

[73] Assignee: Helene Curtis, Inc., Chicago, Ill.

[21] Appl. No.: 08/986,815

[22] Filed: Dec. 8, 1997

[30] Foreign Application Priority Data

Dec. 9, 1996 [GB] United Kingdom .................. 9625562

[51] Int. Cl.$^6$ ............................... A61K 7/32; A61K 7/34; A61K 7/38; A61K 7/00
[52] U.S. Cl. ................................ 424/65; 424/66; 424/68; 424/400; 424/401
[58] Field of Search ................................. 424/65, 66, 68, 424/400, 401

[56] References Cited

U.S. PATENT DOCUMENTS

| 4,822,603 | 4/1989 | Farris et al. | 424/66 |
| 4,863,721 | 9/1989 | Beck et al. | 424/47 |

FOREIGN PATENT DOCUMENTS

94/24995  11/1994  WIPO.

OTHER PUBLICATIONS

European Search Report Application No. PCT EP 97/06,676 dated Apr. 6, 1998.

*Primary Examiner*—Shelley A. Dodson
*Attorney, Agent, or Firm*—Matthew Boxer

[57] ABSTRACT

A suspension antiperspirant composition for topical application to the human skin comprising from 10 to 26% by weight of the composition of a solid particulate antiperspirant active suspended in a cosmetic base, wherein the antiperspirant active comprises a blend of an antiperspirant active with relatively small particles with a volume average particle size in the range of from 0.5 to 8 μm and of an antiperspirant active with relatively large particles having a volume average particle size in the range of larger than 12 to smaller than 50 μm, the weight ratio of the antiperspirant active having smaller particles to the antiperspirant active having larger particles in the composition is in the region of 5:1 to 1:5 by weight.

7 Claims, No Drawings

COSMETIC COMPOSITION

This invention relates to cosmetic compositions in stick form. In particular, it relates to compositions for topical application to the human skin which are antiperspirant compositions. Such stick compositions can typically be used in conjunction with a stick holder for convenience of use. Antiperspirant sticks are known of the emulsion type, where for example an antiperspirant active material is dissolved in an aqueous internal phase of an emulsion. Alternatively, it is known for the antiperspirant active, which is typically a metal salt, such as an aluminium or zirconium salt, to be suspended as small particles in an otherwise solid cosmetic base. Such suspension sticks are typically generally based on a gelling agent such as a waxy material, often in combination with a carrier fluid which is typically an oil material such as a silicone fluid.

One problem associated with suspension sticks is the desire to improve the sensory properties of the product, such as the feel of the product on the skin during application. In such suspension sticks, the volume average particle size of the suspended antiperspirant active material is typically in the range of 0.5 to about 8 μm.

We have found that the incorporation of larger antiperspirant active material particles (i.e. having a volume average particle size larger than about 12 μm and smaller than about 50 μm, and typically in the region of 15 to 25 μm) in such suspension sticks contributes positively to the sensory properties of the cosmetic stick on application. In particular, improved "glide" of the stick on the skin has been observed.

Further we have found that by using a mixture of relatively fine particle size (i.e. volume average particle size 0.5 to 8 μm) and relatively large particle size active (typically of volume average particle size of greater than 12 μm and less than 50 μm, and notably of a volume average particle size of 15 to 25 μm) in such a topical composition provides a sensory benefit compared to a stick containing only the relatively fine particle size active. In particular, we have found that when such a combination of larger and smaller average volume particle size actives is used, a settling of the larger particle size material during manufacture of the product is avoided, thereby avoiding an uneven distribution of the antiperspirant active in the product.

Thus, according to the invention, there is provided a suspension antiperspirant composition for topical application to the human skin comprising a solid particulate antiperspirant active suspended in a cosmetic base, characterised in that the antiperspirant active comprises relatively small particles with an a volume average particle size in the range 0.5 to 8 μm and relatively large particles having a volume average particle size in the range 12 to 50 μm.

Preferably, the ratio of relatively small to relatively large particles in the composition is in the region 5:1 to 1:5 by weight, more preferably in the region 3:1 to 1:3 by weight.

Conveniently, the cosmetic base material of the composition may be based on a mixture of a gelling agent with a carrier fluid, for example a long chain fatty alcohol and a volatile silicone, although the cosmetic base may be any known cosmetic base composition. Where the cosmetic base is a mixture of a long chain fatty alcohol and a volatile silicone, the fatty alcohol may, for example, be $C_8$ to $C_{22}$ fatty alcohol, such as cetyl alcohol, stearyl alcohol, myristyl alcohol, lauryl alcohol, behenyl alcohol, and mixtures thereof. Typically, such long chain fatty alcohols may be present in the composition at a level of 5 to 25% by weight.

Useful volatile silicones in such solid stick compositions may be either cyclic or linear polydimethylsiloxanes, containing 3 to 9, preferably from 4 to 5 silicon atoms. Suitable materials include silicones offered by Dow Corning Corporation, for example, Dow Corning 344, 345 and 200, Union Carbide, including Silicone 7207 and Silicone 7158, and Stauffer Chemical, such as SWS-03314.

Other suitable components of the composition include waxes, such as castor wax, fatty acids, silicone waxes and glycerol monostearate, with levels of the wax typically being in the region of 0.5 to 25% by weight.

Preferably, the composition according to the invention is essentially anhydrous—that is, it comprises less than about 1% by weight of water. The antiperspirant active in the composition may be any known antiperspirant active provided it is suspendible in the composition, but may in particular comprise a metal salt, based on aluminium and/or zirconium. The total amount of antiperspirant active material typically present in the composition is a level of at least 10% by weight or more, in order to provide an antiperspirant benefit. Typically, the composition will contain no more than 26% by weight in total of the antiperspirant active. For further guidance regarding antiperspirant metal actives, a non-limiting list of antiperspirant metal salts is provided by the FDA in "Antiperspirant drug products for over the counter human use, a tentative final monograph", Federal Register 47:36592 (1982).

The volume average particle size of the smaller particle size material is in the region of from 0.5 to 8 μm, and is preferably in the region of from 3 to 6 μm. The volume average particle size of the larger particle size material is in the region of greater than 12 to less than 50 μm, and may preferably be in the region of 12 to 35 μm, more preferably in the region of 15 to 25 μm, most preferably around 18 μm. It is found that at around this volume average particle size optimum sensory benefits are achieved, and that the tendency of the larger particle size material to try to settle is minimised.

Alternatively, the relatively large particle size active can be characterised by measuring the particle size distribution and deriving a peak value of particle size, and mapping out a range of particle size at either side of the peak value at which the population of particles is at least half of the peak particle size, wherein the lower of these so called "half peak height" particle size values is greater than 10 μm.

It is also been found that mixtures of relatively small and relatively large volume average particle size actives in compositions according to the invention often produce more than one peak above 2 μm (i.e. two distinct peaks are visible) when viewed as a distribution of number of particles against particle size using laser scattering techniques.

The volume average particle size of antiperspirant actives used in compositions according to the invention is determined by laser scattering techniques using a light scattering instrument such as a Malvern MasterSizer. A suitable technique used is referred to in "The Basic Principles of Particle Size Analysis" by Dr. Alan Rawle of Malvern Instruments Ltd., Spring Lane South, Malvern, Worcestershire, England.

Antiperspirant materials of differing average volume particle sizes are available as proprietary materials, for example AZG 7167 (ex. Summit, which has a volume average particle size of around 5 μm), AZG 6313 (ex. Summit, which has a volume average particle size of around 18 μm), and Westchlor ZR30B DM HBD (ex. Westwood which has a volume average particle size of around 35 μm).

In a preferred embodiment of the invention, the composition additionally comprises a masking oil, which can typically be present at a level of 3 to 40% by weight of the composition. Suitable masking oils include for example, polydecene, polybutene, PPG-14 butyl ether, non-volatile silicones, isopropyl myristate, isopropyl palmitate, $C_{12}$–$C_{15}$ alkyl benzoates, and mineral oils.

The antiperspirant composition according to the invention may comprise other ingredients, depending on the properties required in the finished product.

Examples of other ingredients which can optionally be present in a cosmetic base in a composition according to the invention include:

cosmetically acceptable vehicles, such as straight and branched chain lower alcohols, for example ethanol, isopropanol, or isobutanol;

non-volatile silicones;

deodorising compounds, including deoperfumes and compounds which can also act as antimicrobial agents, such as unsaturated fatty acids or other antimicrobial agents, e.g. Irgasan DP300, ex Ciba Geigy;

skin feel improvers, such as talc and finely divided polyethylene, an example of which is Acumist B18;

humectants, such as polyols, for example glycerol;

emollients;

sunscreens;

perfumes;

preservatives and antioxidants;

skin benefit agents, such as allantoin;

colours;

skin cooling agents, such as menthol and menthol derivatives;

other cosmetic adjuncts conventionally employed in stick antiperspirant products. The balance of the composition (i.e. 76 to 90% by weight) can typically comprise any of the above components in the cosmetic base.

Compositions according to the invention can typically be prepared by heating the carrier fluid (e.g. volatile silicone) and any gelling agents such as waxes to 80° C., and stirring the molten mixture. The powder components of the composition are then added (e.g. antiperspirant active materials, talc) and thoroughly mixed. The composition is then cooled to 65° C., and any perfume is added. The composition is then cooled to 58° C., and poured into stick barrels and then further cooled to form a solid stick.

The invention will now be further described, by way of example only.

COMPOSITIONS

The following compositions are prepared according to the method described above, and are according to the invention:

| Component | 1 | 2 | 3 |
|---|---|---|---|
| Zr/Al antiperspirant active (1) | 12.0 | 6.0 | 18.0 |
| Zr/Al antiperspirant active (2) | 12.0 | 18.0 | 6.0 |
| Stearyl alcohol (3) | 14.0 | 14.0 | 14.0 |
| Hydrogenated Castor Oil (4) | 4.0 | 4.0 | 4.0 |
| PEG 8 Distearate (5) | 1.0 | 1.0 | 1.0 |
| Talc (6) | 3.2 | 3.2 | 3.2 |
| Volatile Silicone (7) | 52.8 | 52.8 | 52.8 |
| Perfume | 1.0 | 1.0 | 1.0 |

Unless specifically mentioned, all amounts are percentages by weight of the composition.

(1)—volume average particle size of around 5 μm, ex. Summit (2)—volume average particle size of around 18 μm, ex. Summit (3)—Lorol C18 Deo, ex Henkel (4)—Castorwax MP80, ex Caschem (5)—Estol EO4DS3724, ex Unichema (6)—Suprafino talc, ex Cyprus Industries (7)—DC 345, ex Dow Corning Test Sticks according to the above compositions, together with a standard antiperspirant stick (in which all of the antiperspirant active had a volume average particle size of less than 8 μm) and one in which all of the active was of larger particle size (in the region 16–20 μm) were assessed for the distribution of the antiperspirant active in the stick, and also panel tested on volunteers for smoothness on application.

The method of determination of concentration of antiperspirant active in different parts of the stick is by conductivity measurements, which involves immersion of a given weight of a product from a part of the stick (i.e. top, medium or bottom) in a controlled temperature water bath, and measuring the conductivity. An increased level of conductivity indicates a higher concentration of ions in solution, which in turn relates to the level of antiperspirant active material present in that segment of stick.

Conductivity measurements carried out on the stick containing solely larger average volume particle size (i.e. 16–20 μm) active indicated that a degree of settling of the active had occurred in the time it took for the stick to solidify, and hence there was a deficiency of antiperspirant active in one part of the stick. However, conductivity measurements indicate that this sedimentation problem was alleviated with compositions 1–3 containing blends of larger and smaller particle size active materials.

In addition, as indicated by the below average panel score, compositions comprising blends of antiperspirant active materials of different average volume particle size demonstrated improved smoothness on application over a standard stick containing only fine (less than 8 μm) active material, and a similar degree of smoothness as the stick containing only 16–20 μm active.

| Stick | Smoothness Score |
|---|---|
| "Standard" (0.5–8 μm active) | 43 |
| Stick containing 16–20 μm active | 62 |
| Composition 1 | 59 |
| Composition 2 | 63 |
| Composition 3 | 72 |

This analysis was carried out using the established Descriptive Sensory Analysis methodology (Stone, H & Sidel, JL; Sensory Evaluation Practices, Academic Press, Inc. 1985) in which sensory properties are assessed using a panel of trained judges to assess a range of well defined sensory attributes. A score of zero indicates minimum smoothness while a score of 100 indicates maximum smoothness.

We claim:

1. A suspension antiperspirant composition for topical application to the human skin comprising from 10 to 26% by weight of the composition of a solid particulate antiperspirant active suspended in a cosmetic base, wherein the antiperspirant active comprises a blend (a) of an antiperspirant active with relatively small particles with a volume average particle size in the range of from 0.5 to 8 μm and (b)

of an antiperspirant active with relatively large particles having a volume average particle size in the range of larger than 12 to smaller than 50 μm, the weight ratio of the antiperspirant active having smaller particles to the antiperspirant active having larger particles in the composition is in the region of 5:1 to 1:5 by weight.

2. A suspension antiperspirant composition according to claim 1, wherein the antiperspirant active (b) has a particle size of 12 to 35 μm.

3. A suspension antiperspirant composition according to claim 1, wherein the antiperspirant active (b) has a particle size of 12 to 25 μm.

4. A suspension antiperspirant composition according to claim 1, wherein the ratio of smaller particles to larger particles is in the region 3:1 to 1:3 by weight.

5. A suspension antiperspirant composition according to claim 1, wherein the antiperspirant active comprises 10–26% by weight of the composition.

6. A suspension antiperspirant composition according to claim 1, additionally comprising a masking oil.

7. A suspension antiperspirant composition according to claim 1, wherein the composition is essentially anhydrous.

* * * * *